United States Patent [19]

Vermot

[11] Patent Number: 5,165,425
[45] Date of Patent: Nov. 24, 1992

[54] METHOD OF FORMING A FLAP OF TISSUE

[75] Inventor: Jerome J. H. Vermot, Mougins-Le-Haut, France

[73] Assignee: Dow Corning France S.A., Valbonne, France

[21] Appl. No.: 815,596

[22] Filed: Dec. 27, 1991

Related U.S. Application Data

[63] Continuation of Ser. No. 545,325, Jun. 27, 1990, abandoned.

[51] Int. Cl.⁵ .............................................. A61B 17/00
[52] U.S. Cl. .................................... 128/898; 128/899; 606/1; 606/99
[58] Field of Search ............... 606/1, 192, 99, 195; 128/898, 899; 623/8, 37, 11

[56] References Cited

U.S. PATENT DOCUMENTS

| | | | |
|---|---|---|---|
| 3,371,664 | 3/1968 | Pleshette | 128/127 |
| 3,902,198 | 9/1975 | Rathjen | 623/8 |
| 4,095,295 | 6/1978 | Lake | 623/8 |
| 4,416,267 | 11/1983 | Garren et al. | 606/192 X |
| 4,545,373 | 10/1985 | Christoudias | 128/303 R |
| 4,648,383 | 3/1987 | Angelchik | 128/899 |
| 4,651,717 | 3/1987 | Jakubczak | 606/192 X |
| 4,679,556 | 7/1987 | Lubock et al. | 606/1 |
| 4,769,036 | 9/1988 | Modir | 623/8 |
| 4,802,479 | 2/1989 | Haber et al. | 606/192 |

FOREIGN PATENT DOCUMENTS

| | | |
|---|---|---|
| 0260080 | 3/1988 | European Pat. Off. |
| 443418 | 4/1927 | Fed. Rep. of Germany |
| 2608916 | 12/1986 | France |
| 512456 | 9/1939 | United Kingdom ............... 606/192 |

Primary Examiner—Michael H. Thaler
Attorney, Agent, or Firm—John L. Chiatalas

[57] ABSTRACT

The specification describes and claims a flexible article intended for inflation in the human or animal body, e.g. a prosthesis or tissue expander, which comprises an envelope having upon its surface a receptor structure adapted to receive a portion of a tool intended for inserting the article into a subcutaneous cavity in the body and capable of releasing the tool when the article has been inserted subcutaneously in the body. Preferably the receptor structure comprises an abutment portion against which an end portion of the tool may bear during insertion of the article into the cavity and location indicator whereby the end portion of the tool is restrained in contact with the abutment portion during the insertion. The preferred article is an elongate tissue expander and the receptor structure is located adjacent an end portion of the envelope with its abutment portion located nearer to the end portion than the location means. Tools for use with articles of the invention are described. The preferred article may be used to form a flap of tissue on a human or animal body by inserting into the cavity a tool of sufficient length that its distal end portion can penetrate the cavity to its furthermost extremity, on which a tissue expander according to the invention is mounted, disengaging the from the receptor structure and inflating the envelope of the tissue expander progressively to induce formation of flap tissue.

2 Claims, 1 Drawing Sheet

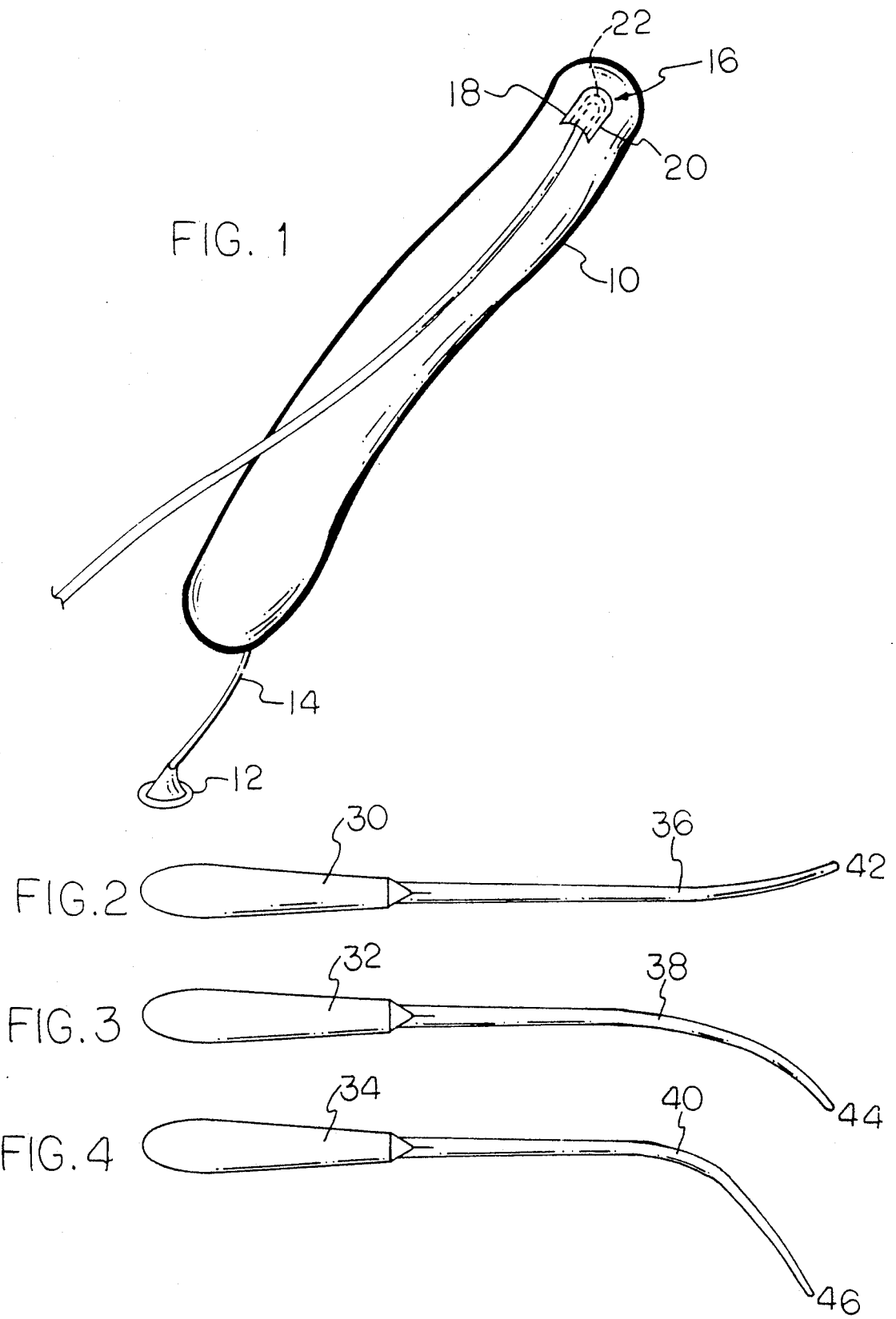

METHOD OF FORMING A FLAP OF TISSUE

This is a continuation of application Ser. No. 545,325, filed on Jun. 27, 1990, now abandoned.

This invention is concerned with means for surgical treatment of the human or animal body.

In the surgical treatment of the human body it is a practice to insert into the body articles of a flaccid nature, for example certain prostheses which are placed to mimic natural organs, and tissue expanders which are used to generate a flap of tissue which may be required for treatment of the body, or to generate a cavity into which a prosthesis may be inserted. There are many designs of prostheses available some of which comprise a flexible envelope at least partially filled with a fluid which inherently is not shape retaining but which are intended to be inflated using, for example, saline fluid. Various designs of tissue expander are available. Generally they comprise an inflatable envelope which is implanted in the body and progressively inflated over an extended period of time, for example a period of several weeks or months. The envelope is generally of a flaccid nature and, especially when collapsed i.e. completely deflated, is highly flexible. The steps of insertion of such articles into a cavity formed to accept it in the body and manipulation of the article within the cavity to obtain correct location can be difficult due to the flexibility of the article. The operation is especially difficult when there are limitations on the visibility of the operation or on space for handling of the article within the cavity. Such limitations may arise for example from the location or dimensions, for example extreme length, of the cavity into which the article is placed or from a restricted incision through which it is to be inserted into the cavity. The difficulties are important in relation to placement of, for example partially filled prostheses, where the desired cosmetic effect influences the decision to employ a small entry incision, but are especially evident in the case of tissue expanders employed to expand tissue required for provision of a flap of unscarred tissue, where the need for unscarred tissue precludes placement of the expander through an incision which would lie within the flap.

We have now found that one may insert and dispose a flaccid article subcutaneously into the human or animal body for inflation more readily than was possible heretofore by providing the article with means adapted to receive a tool by means of which the article may be urged through an incision in the body to locate the article in the body.

The present invention provides in one of its aspects a flexible article intended for disposition subcutaneously in the human or animal body for inflation which comprises an envelope having upon its surface receptor means adapted to receive a portion of a tool intended for inserting the article into a subcutaneous cavity in the body and capable of releasing the tool when the article has been inserted subcutaneously in a human or animal body.

A flexible article according to the invention is initially flaccid and floppy and is adapted to be inflated and swelled to a desired shape and volume in the body and may be, for example, a prosthesis or a tissue expander. A prosthesis according to the invention may contain some gel like material or saline fluid and may be constructed so that when inflated it mimics, for example a female breast. Means are provided for inflating the prosthesis when in the body. A tissue expander according to the invention may comprise an envelope which is intended to be inflated for example with saline fluid. The envelope of an article according to the invention may be formed from any of those biocompatible materials, for example a biocompatible silicone elastomer, employed in the commercially available tissue expanders. The envelope may be formed in known manner, for example by deposition of a silicone material on a mandrel followed by curing of the silicone to an elastomeric state. The envelope may be designed to assume any desired shape when filled. In an article according to the invention in the form of a tissue expander, hereinafter described to illustrate the invention, the envelope is of an elongate shape and is suitable for insertion in an elongate cavity open at one end only thereof. Such expanders are in demand, for example for use in provision of an elongate flap of body tissue at the extremity of a limb for reconstructive surgery.

An article according to the invention has receptor means adapted to receive a portion of a tool intended for inserting the article into a subcutaneous cavity in the body and capable of releasing the tool when the article has been inserted subcutaneously in a human or animal body. Preferably, the receptor means comprises an abutment portion against which an end portion of the tool may bear during insertion of the article into the cavity, and location means whereby said end portion of the tool is restrained in contact with the abutment portion during the insertion. The abutment portion serves to allow the article to be pushed into the cavity by pushing on the tool which contacts the abutment portion. The location means may comprise for example, wall elements upstanding from the envelope and which are spaced apart sufficiently to receive the tool between them, but not so far apart that the tool is allowed to disengage from the abutment portion whilst pressure is being exerted on the tool to insert the article in the cavity. When the article is elongate the receptor means is preferably located adjacent an end portion of the envelope with the abutment portion located nearer to said end portion than said location means. In the illustrative article, the receptor means is provided by a pocket integral with the surface of the envelope and which comprises two side edges, which are at least substantially parallel to each other, and an end wall extending between them. In this embodiment an end wall of the pocket provides aid abutment means and the inner surface of the pocket, together with the enclosed outer surface of the envelope, provide said location means. The side edges are spaced apart so that the end portion of the tool is snugly received in the pocket to an extent sufficient to retain the tool in the pocket during the stage of urging the article into the cavity Conveniently, the pocket is located adjacent an edge or end portion of the envelope with an open mouth portion of the pocket directed away from that end portion. The pocket may be formed by securing a portion of a foil of biocompatible silicone elastomer to the envelope in the desired location. This may conveniently be done by locating a foil of uncured silicone elastomer upon the envelope before the envelope is cured and then curing the silicone elastomer of the envelope and the foil simultaneously.

An article according to the invention, e.g. in the form of a tissue expander, is provided with valve means through which inflating medium under pressure may be introduced from time to time into the envelope by means of a syringe or pump. The valve means may comprise, for example, a permanently attached self sealing valve secured in the envelope wall, or a remote self-sealing valve connected with the envelope by means of a feeder tube permanently attached to the valve and envelope.

An article according to the invention may be introduced through a small incision into a cavity prepared in the body by inserting through the incision a tool of sufficient length that its distal end portion can penetrate the cavity to its furthermost extremity, the tool having an article according to the invention mounted upon its distal end portion by means of the receptor means upon the surface of the envelope, urging the distal end portion of the tool into the cavity until the distal end portion is adjacent the furthermost extremity of the cavity, disengaging the distal end portion of the tool from the receptor means and removing the tool from the cavity.

An article according to the invention in the form of a tissue expander may be used, for example to form a flap of tissue on a human or animal body by a procedure which includes, inter alia, inserting an implement through the skin and working the implement to induce a subcutaneous cavity, withdrawing the implement from the body, inserting into the cavity a tool of sufficient length that its distal end portion can penetrate the cavity to its furthermost extremity, the tool having a tissue expander according to the invention mounted upon its distal end portion by means of the receptor means upon the surface of the envelope, urging the distal end portion of the tool through the cavity until the distal end portion is adjacent the furthermost extremity of the cavity, disengaging the distal end portion of the tool from the receptor means, removing the tool from the cavity and inflating the envelope of the tissue expander progressively to induce formation of flap tissue.

In order that the invention may become more clear, there now follows a detailed description to be read with the accompanying drawings of the illustrative article and of tools for use therewith. In the drawings:

FIG. 1 is an elevation of the illustrative article,
FIG. 2 is an elevation of a first tool,
FIG. 3 is an elevation of a second tool and
FIG. 4 is an elevation of a third tool.

The illustrative article is a tissue expander and comprises a flexible envelope (10) and a remote self-sealing valve (12) connected with the envelope by means of a feeder tube (14) permanently attached to the envelope and the valve. The envelope (10) is intended to be expanded by periodic inflation with saline fluid. It is formed from a biocompatible silicone elastomer by deposition of a silicone material on a mandrel followed by curing of the silicone to an elastomeric state. The envelope is of an elongate shape and is suitable for insertion in an elongate cavity open at one end only thereof.

Receptor means in the form of a pocket (16) is formed on the surface of the envelope adjacent one end thereof. The pocket, which is pod-like and has a part circular opening for receiving a tool, is bounded by two upstanding side walls which are joined together and subtend from edges (18, 20) which are at least substantially parallel to each other, and an end wall (22) extending between them. The end wall of the pocket provides abutment means against which a tool may bear during insertion of the article into the cavity. The inner surface of the pocket side walls, together with the enclosed outer surface of the envelope, provide location means whereby the end portion of the tool is restrained in contact with the end wall during the insertion. The side edges (18, 20) are spaced apart so that the end portion of the tool is snugly received in the pocket between the side walls to an extent sufficient to retain the end portion of the tool in the pocket during the stage of urging the article into the cavity. The pocket is located adjacent an end portion of the envelope with its open mouth directed away from that end portion. The pocket is formed by securing a portion of a foil of uncured silicone elastomer upon the envelope before the envelope is cured, and then curing the silicone elastomer of the envelope and the foil simultaneously.

In FIGS. 2, 3 and 4 there are shown tools suitable for use with an article according to the invention. Each of the tools is formed from stainless steel and comprises a handle portion (30, 32, 34) and a probe portion. The probe portions are at least substantially rigid, have curved end portions, are free of sharp edges and have smoothly rounded distal ends (42, 44, 46). As is apparent from the drawings the curvatures of end portions of each of the probes differ one from another. The curvature of the probe of the tool shown in FIG. 2 is selected to facilitate placement of an article according to the invention in the extremity of a leg or arm. The curvature of the probe of the tool shown in FIG. 3 is selected to facilitate placement of an article according to the invention in the thorax. The curvature of the probe of the tool shown in FIG. 4 is selected to facilitate placement of an article according to the invention in the head or neck.

In one method of using the illustrative tissue expander according to the invention, an implement (for example one of the tools shown in FIGS. 2, 3 and 4) is inserted through an incision in the skin and worked around, beneath the skin, to cause the implement to induce a subcutaneous cavity extending for several centimeters. When a cavity of sufficient length has been made the implement is withdrawn from the body, through the incision, and the same instrument or another used as a tool for insertion of the article into the cavity. When the cavity is formed at the end of an arm or leg we prefer to employ the tool shown in FIG. 2. The illustrative tissue expander is mounted upon the distal end of the tool by means of the pocket (16) and the end portion of the tool thrust into the cavity. The tool is then pushed further into the cavity to push the pocket forward and to draw trailing portions of the article into the cavity. Pressure is exerted until the distal end portion of the tool is adjacent the furthermost extremity of the cavity. The distal end portion of the tool is disengaged from the pocket and the tool is removed from the cavity. The valve may then be located on the body and saline solution introduced by means of a hypodermic needle through the valve to the tube (14) and thence to the envelope. Inflation of the envelope is accomplished by introduction of saline solution to the envelope from time to time over a period of several weeks. When sufficient flap tissue has been induced the envelope is deflated and removed from the cavity ready for incision of the tissue.

That which is claimed is:

1. A method of forming a flap of tissue on a mammalian body comprising the steps of:
   (a) providing and inserting an implement through the skin and forming a subcutaneous cavity, then withdrawing the implement from the body;

(b) providing a tool having a length such that a distal end of the tool is capable of penetrating the cavity a distance equivalent to the length of the prosthesis;

(c) providing a flaccid tissue expander formed of a biocompatible elastomer including an envelope having inwardly and outwardly facing surfaces and a pocket integral with the outwardly facing surface of the envelope;

(d) mounting the tissue expander on the distal end of the tool by engaging the distal end of the tool with the receptor means;

(e) urging the distal end of the tool through the cavity to the furthest extremity thereof;

(f) disengaging the distal end of the tool from the receptor means;

(g) removing the tool from the cavity; and (h) inflating the envelope of the tissue expander progressively to induce formation of the flap tissue.

2. The method of claim 1 wherein step (b) further comprises providing the tool with a probe which is substantially rigid, has a curved end, is free of sharp edges and has a smoothly rounded head.

* * * * *